United States Patent
Kang et al.

(10) Patent No.: US 6,632,410 B2
(45) Date of Patent: Oct. 14, 2003

(54) SOLVENT EXTRACTION PROCESS

(75) Inventors: Sang I. Kang, Fort Washington, PA (US); Phillip L. Mattison, Cincinnati, OH (US); Michael J. Virnig, Tucson, AZ (US); R. Brantley Sudderth, Tucson, AZ (US); George A. Wolfe, Tucson, AZ (US)

(73) Assignee: Cognis Corporation, Gulph Mills, PA (US)

( * ) Notice: Subject to any disclaimer, the term of this patent is extended or adjusted under 35 U.S.C. 154(b) by 0 days.

(21) Appl. No.: 09/891,162

(22) Filed: Jun. 25, 2001

(65) Prior Publication Data

US 2001/0055553 A1 Dec. 27, 2001

Related U.S. Application Data

(63) Continuation of application No. 09/635,308, filed on Aug. 9, 2000, now abandoned.
(60) Provisional application No. 60/148,492, filed on Aug. 12, 1999.

(51) Int. Cl.[7] ............................................. C22B 15/00
(52) U.S. Cl. ......................................... 423/24; 210/634
(58) Field of Search ........................... 423/24; 210/634, 210/638

(56) References Cited

U.S. PATENT DOCUMENTS

| | | | |
|---|---|---|---|
| 3,950,488 A | | 4/1976 | Skarbo et al. |
| 4,085,146 A | | 4/1978 | Beswick |
| 4,336,231 A | * | 6/1982 | Dalton ........................ 423/24 |
| 4,507,268 A | | 3/1985 | Kordosky et al. |
| 4,544,532 A | | 10/1985 | Kordosky et al. |
| 4,582,689 A | | 4/1986 | Kordosky |
| 4,957,714 A | * | 9/1990 | Olafson et al. ................ 423/24 |
| 5,015,448 A | | 5/1991 | Vorlop et al. |
| 5,024,821 A | * | 6/1991 | Greenshields et al. ......... 423/24 |
| 5,196,095 A | * | 3/1993 | Sudderth et al. ............... 423/24 |
| 5,281,336 A | * | 1/1994 | Dalton et al. .................. 423/24 |
| 5,399,761 A | | 3/1995 | Levin |
| 5,494,649 A | | 2/1996 | Fristad et al. |
| 5,976,218 A | | 11/1999 | Virnig et al. |

FOREIGN PATENT DOCUMENTS

WO  WO 99/10546  3/1999

OTHER PUBLICATIONS

Zeger, et al., Synthesis and study of extraction agents for copper recovery, Trudy, No. 71, pp. 129–132, 1972, no month.*
Warshawsky, et al., Transition Metal–Chelating Phase Transfer Agents From 3,4–Disubstituted Benzylhalides, Israel J. Chem., vol. 26, pp. 48–55, 1985, no month.*
Translation of Zeger, et al. Russian journal article above, no date.*

* cited by examiner

*Primary Examiner*—Steven Bos
(74) *Attorney, Agent, or Firm*—John E. Drach

(57) ABSTRACT

Copper is preferentially extracted from iron in an aqueous feedstock solution containing dissolved copper and iron values by contacting the feedstock solution with a water-immiscible organic solution comprised of a hydrocarbon solvent and a compound of the formula I

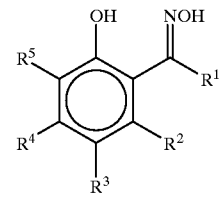

wherein $R^5$ is a $C_{1-22}$ linear or branched alkyl group, a $C_{2-22}$ linear or branched alkenyl group, a $C_6$ aryl group, a $C_{7-22}$ aralkyl group, a halogen, OH or —$OR^6$ wherein $R^6$ is a $C_{1-22}$ linear or branched alkyl group, a $C_{2-22}$ linear or branched alkenyl group, a $C_6$ aryl group, a $C_{7-22}$ aralkyl group; $R^1$ is hydrogen, or a $C_{1-22}$ linear or branched alkyl or alkenyl group, a $C_6$ aryl group or a $C_{7-22}$ aralkyl group; $R^2$–$R^4$ is hydrogen, halogen, a linear or branched $C_{6-12}$ alkyl group, —$OR^6$ wherein $R^6$ is a $C_{1-22}$ linear or branched alkyl group, a $C_{2-22}$ linear or branched alkenyl group, a $C_6$ aryl group, or a $C_{7-22}$ aralkyl group to form an aqueous phase comprised of iron and an organic phase comprised of the hydrocarbon solvent and a copper-extractant complex wherein the copper-extractant complex is soluble in the hydrocarbon solvent. The $R^2$–$R^5$ groups are chosen so that the copper-extractant complex is soluble in the hydrocarbon solvent. After the extraction stage is completed and the organic and aqueous phases separate, the organic phase is substantially free of iron and/or an iron-extractant complex.

8 Claims, No Drawings

SOLVENT EXTRACTION PROCESS

CROSS-REFERENCE TO RELATED APPLICATIONS

This application is a continuation of application Ser. No. 09/635,308, filed on Aug. 09, 2000, now abandoned, which application claims the benefit of copending provisional application Serial No. 60/148,492, filed on Aug. 12, 1999, the entire contents of each of which are incorporated herein by reference.

STATEMENT REGARDING FEDERALLY SPONSORED RESEARCH OR DEVELOPMENT

Not Applicable.

BACKGROUND OF THE INVENTION

The present invention relates generally to solvent extraction processes for recovery of metal values from aqueous solutions and, more particularly, to a method of separating copper from iron resulting in a large improvement in the recovery of copper over iron.

Copper is generally obtained from its ore by a solvent extraction process wherein copper is in an aqueous leach solution obtained from a body of ore which contains a mixture of metals in addition to copper. The leaching medium dissolves salts of copper and other metals as it trickles through the ore, to provide an aqueous solution of the mixture of metal values. The metal values are usually leached with sulfuric acid medium, providing an acidic aqueous solution. The aqueous solution is mixed in tanks with an extraction reagent which is dissolved in an organic solvent, e.g., a kerosene. The reagent includes an extractant chemical which forms a metal-extractant complex with the copper ions in preference to ions of other metals. The step of forming the complex is called the extraction or loading stage of the solvent extraction process. The outlet of the mixing tanks is continuously fed to a large settling tank, where the organic solvent or organic phase, now containing the copper-extractant complex in solution, is separated from the depleted aqueous solution or aqueous phase. This part of the process is called phase separation. Usually, the process of extraction is repeated through two or more mixer-settler stages, in order to more completely extract the copper.

Among the more problematic copper bearing feedstocks treated in conventional solvent extraction processes are those in which quantities of dissolved iron values range from about 1 gpl or 20 gpl. Frequently the extractant chemical employed will form an iron-extractant complex which, in turn, results in the presence of iron in the strip aqueous phase. Where electrowinning is employed to recover copper from the strip aqueous solution, the presence of iron will complicate recovery by decreasing current efficiency. To avoid such problems, a more or less constant "bleed" of the tankhouse solution is established, with the solution bled off being circulated back into the initial feedstock or to the leach pile itself. Because such tankhouse bleed solutions contain appreciable amounts of copper and acid, efficiency of the entire system can be compromised.

The currently more favored reagents employed in recovery of copper values from aqueous solutions having iron values present are those which exhibit a relatively high degree of copper/iron selectivity, i.e., those which, under standard operating conditions, extract a high proportion of the copper present in the feedstock but only a minor proportion of the iron present. Among the reagents credited with displaying good copper/iron selectivity characteristics are those including hydroxy aryl oxime extractants such as long chain alkyl or alkenyl solubilized hydroxy aryl aldoximes and ketone oximes. See, for example, Birch, "The Evaluation of the New Copper Extractant 'P-1'" appearing in the Proceedings of the 1974 International Solvent Extraction Conference, pp. 2837–2871, wherein "high selectivity against Fe (III) . . . in the sulphate system" is attributed to a reagent containing a 2-hydroxy-5-nonyl benzaldoxime extractant. Ketoximes such as 2-hydroxy-5-alkylphenyl ketoximes have also been used to selectively remove copper as described in U.S. Pat. No. 5,670,035, the entire contents of which are incorporated herein by reference. Each of the above-noted hydroxy aryl oxime-containing reagents has proven to extract undesirable amounts of iron from copper and iron-bearing ores. As a result, recovery of copper from such solutions necessitates at least some bleeding off of tankhouse solutions with losses to the overall economy of the system. Thus, there is a need to selectively remove copper to the more complete exclusion of iron from aqueous solutions containing copper and iron.

SUMMARY OF THE INVENTION

One aspect of the present invention pertains to a process for the separation of copper from iron in an aqueous feedstock solution containing dissolved copper and iron values comprising contacting the feedstock solution with a water-immiscible organic solution comprised of a hydrocarbon solvent and a compound of the formula I

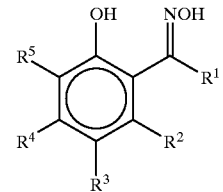

wherein $R^5$ is a $C_{1-22}$ linear or branched alkyl group, a $C_{2-22}$ linear or branched alkenyl group, a $C_6$ aryl group, a $C_{7-22}$ aralkyl group, a halogen, OH or —$OR^6$ wherein $R^6$ is a $C_{1-22}$ linear or branched alkyl group, a $C_{2-22}$ linear or branched alkenyl group, a $C_6$ aryl group, a $C_{7-22}$ aralkyl group; $R^1$ is hydrogen, or a $C_{1-22}$ linear or branched alkyl or alkenyl group, a $C_6$ aryl group or a $C_{7-22}$ aralkyl group; $R^2$–$R^4$ is hydrogen, halogen, a linear or branched $C_{6-12}$ alkyl group, —$OR^6$ wherein $R^6$ is a $C_{1-22}$ linear or branched alkyl group, a $C_{2-22}$ linear or branched alkenyl group, a $C_6$ aryl group, or a $C_{7-22}$ aralkyl group to form an aqueous phase comprised of iron and an organic phase comprised of the hydrocarbon solvent and a copper-extractant complex wherein the copper-extractant complex is soluble in the hydrocarbon solvent. The $R^2$–$R^5$ groups are chosen so that the copper-extractant complex is soluble in the hydrocarbon solvent. After the extraction stage is completed and the organic and aqueous phases separate, the organic phase is substantially free of iron and/or an iron-extractant complex.

Another aspect of the invention pertains to novel ketoximes which are useful as extractants for copper and which are compounds of the formula II

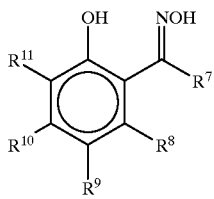

wherein $R^{11}$ is a $C_{1\text{-}22}$ linear or branched alkyl group, a $C_{2\text{-}22}$ linear or branched alkenyl group, a $C_6$ aryl group, a $C_{7\text{-}22}$ aralkyl group, a halogen, OH or —$OR^6$ wherein $R^6$ is a $C_{1\text{-}22}$ linear or branched alkyl group, a $C_{2\text{-}22}$ linear or branched alkenyl group, a $C_6$ aryl group, a $C_{7\text{-}22}$ aralkyl group; $R^7$ is a $C_{1\text{-}22}$ linear or branched alkyl or alkenyl group, a $C_6$ aryl group or a $C_{7\text{-}22}$ aralkyl group; branched alkyl group, a $C_{2\text{-}22}$ linear or branched alkenyl group, a $C_6$ aryl group, a $C_{7\text{-}22}$ aralkyl group, a halogen, OH or —$OR^{12}$ wherein $R^{12}$ is a $C_{1\text{-}22}$ linear or branched alkyl group, a $C_{2\text{-}22}$ linear or branched alkenyl group, a $C_6$ aryl group, a $C_{7\text{-}22}$ aralkyl group; $R^7$ is a $C_{1\text{-}22}$ linear or branched alkyl group, a $C_{2\text{-}22}$ linear or branched alkenyl group, a $C_6$ aryl group or a $C_{7\text{-}22}$ aralkyl group; $R^8$–$R^{10}$ is hydrogen, halogen, a linear or branched $C_{6\text{-}12}$ alkyl group, —$OR^{12}$ wherein $R^{12}$ is a $C_{1\text{-}22}$ linear or branched alkyl group, a $C_{2\text{-}22}$ linear or branched alkenyl group, a $C_6$ aryl group, or a $C_{7\text{-}22}$ aralkyl group with the proviso that the total number of carbon atoms in $R^8$–$R^{10}$ is at least 7.

BRIEF DESCRIPTION OF THE SEVERAL VIEWS OF THE DRAWING

Not Applicable.

DETAILED DESCRIPTION

In the process for the separation of copper from iron in an aqueous feedstock solution containing dissolved copper and iron values, the feedstock solution is contacted with a water-immiscible organic solution comprised of a hydrocarbon solvent and a compound of the formula I

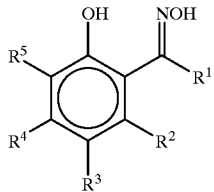

wherein $R^5$ is a $C_{1\text{-}22}$ linear or branched alkyl group, a $C_{2\text{-}22}$ linear or branched alkenyl group, a $C_6$ aryl group, a $C_{7\text{-}22}$ aralkyl group, a halogen, OH or —$OR^6$ wherein $R^6$ is a $C_{1\text{-}22}$ linear or branched alkyl group, a $C_{2\text{-}22}$ linear or branched alkenyl group, a $C_6$ aryl group, a $C_{7\text{-}22}$ aralkyl group; $R^1$ is hydrogen, or a $C_{1\text{-}22}$ linear or branched alkyl or alkenyl group, a $C_6$aryl group or a $C_{7\text{-}22}$ aralkyl group; $R^2$–$R^4$ is hydrogen, halogen, a linear or branched $C_{6\text{-}12}$ alkyl group, —$OR^6$ wherein $R^6$ is a $C_{1\text{-}22}$ linear or branched alkyl group, a $C_{2\text{-}22}$ linear or branched alkenyl group, a $C_6$ aryl group, or a $C_{7\text{-}22}$ aralkyl group to form an aqueous phase comprised of iron and an organic phase comprised of the hydrocarbon solvent and a copper-extractant complex wherein the copper-extractant complex is soluble in the hydrocarbon solvent. The $R^2$–$R^5$ groups are chosen so that the copper-extractant complex is soluble in the hydrocarbon to the extent of at least about 1 g/l Cu solubility, preferably at least 5 g/l.

The compounds of the formula I that can be used in the process according to the invention can be made by a number of different methods known to those skilled in the art. For example, 3-methyl-5-nonylsalicylaldoxime can be made by reacting o-cresol with tripropylene in the presence of an acid catalyst such as AMBERLYST® 15 resin to form 4-nonyl-2-cresol which is in turn converted to the aldehyde by reaction with para-formaldehyde in the presence of a catalyst such as titanium cresylate. The 3-methyl-5-nonylsalicylaldehyde is then reacted with hydroxylamine sulfate to form the 3-methyl-5-nonylsalicylaldoxime. In all cases, the total number of carbon atoms in all of $R^2$–$R^5$ groups must be great enough so that the corresponding copper-extractant complex is soluble in the hydrocarbon solvent.

The hydrocarbon solvent can be any liquid organic compound having a dielectric constant of up to about 2.5. Examples of such liquids include, but are not limited to, liquid alkanes such as pentane, hexane, heptane, octane, nonane; liquid aromatic compounds such as benzene, toluene, o-, m- and, p-xylene. Preferred solvents are those having flash points of about 150° F. or higher and solubilities in water of less than about 0.1.

The feedstock solution containing dissolved copper and iron values is contacted with the water-immiscible organic solution comprised of a hydrocarbon solvent as described herein and a compound of the formula I for a period of time sufficient to allow the oxime described herein to a form complex with the iron and copper ions. The feedstock can be contacted by the organic solution in any manner that brings the two immiscible phases together for a period of time sufficient to allow the compounds of formula I to a form complex with the iron and copper ions. This includes shaking the two phases together in a separatory funnel or mixing the two phases together in a mix tank as described in U.S. Pat. No. 4,957,714, the entire contents of which is incorporated herein by reference.

While not wishing to be bound by theory, it is believed that the increased copper/iron selectivity of the process according to the invention is due to the decreased stability of the iron complex of the 3-substituted oximes relative to the corresponding copper complex. This stability difference is related to the structure of the oximes of formula I. The copper complexes of the 3-substituted oximes are more stable than the iron-complexes of the 3-substituted oximes. This stability difference is not as great in copper and iron complexes of oximes of the formula I that are unsubstituted at the 3-position (wherein $R^5$ is hydrogen). Since the iron complex is less stable for the 3-substituted oximes, it is present in a relatively low concentration.

The process according to the invention is also applicable to systems wherein the aqueous feedstock is a concentrate leach solution and/or a bioleach solution. These solutions tend to have higher acid concentrations as described in U.S. Pat. Nos. 5,698,170 and 5,895,633, the entire contents of each of which is incorporated herein by reference, and in many cases higher iron concentrations than most current oxide heap leach solutions. The 3-methyl ketoximes as described herein are especially preferred for such applications.

The following examples are meant to illustrate but not to limit the invention.

EXAMPLE 1

Preparation of 4-Nonyl-2-cresol (1a)

o-Cresol (108 g, 1 mol), tripropylene (131.74 g), and Amberlyst 15 (8.55 g) were stirred for 20 h at 75° C. and 2 h at 90° C. At ambient temperature the reaction mixture was mixed with heptanes and filtered to remove the catalyst. Removal of the solvent in vacuo gave crude product (225.23 g), which was distilled to obtain pure 4-nonyl-2-cresol (203.76 g) in 87% yield.

EXAMPLE 2

Preparation of 3-Methyl-5-nonylsalicylaldehyde (1b)

To toluene (500 mL) in a 2-l Parr pressure reactor at 220° C. was added a slurry of 4-nonyl-2-cresol (1a) (234 g, 1 mol), titanium(IV) cresylate (2 mL) and powder paraformaldehyde (83 g, 2.8 mol) for 10 mins. maintaining the temperature at 210–220° C. The reaction was kept for additional 20 mins. Crude product was collected in an expansion tank and the residue in the pressure reactor washed with toluene (200-mL×2). Combined toluene phases were concentrated in vacuo. The resulting viscous dark amber liquid was distilled in vacuo to obtain 3-methyl-5-nonylsalicylaldehyde (183 g) in 70% yield.

EXAMPLE 3

Preparation of 3-Methyl-5-nonylsalicylaldoxime (1c)

3-Methyl-5-nonylsalicylaldehyde (1b) (570.8 g, 2.18 mol) was treated with hydroxylamine sulfate (197 g, 1.2 mol) and anhydrous sodium acetate (197 g, 2.40 mol) in methanol (1.5 L) at reflux for 16.5 h. Crude product in the solvent was filtered and concentrated to obtain 3-methyl-5-nonylsalicylaldoxime (595.45 g) in 98.6% yield.

EXAMPLE 4

Preparation of 4-Nonyl-2-methylphenyl Acetate (2a)

4-Nonyl-2-cresol (1a) (934 g, 3.99 mol) was treated with acetic anhydride (456.6 g, 4.42 mol) in the presence of a few drops of concentrated sulfuric acid at 110° C. for 1 h. After cooling to ambient temperature, the reaction mixture was transferred into a 4-l separatory funnel with aid of heptane (400 mL). The resulting organic phase was washed with aqueous sodium bicarbonate solution and water until the pH became 6 or so. The heptane phase was dried over sodium sulfate and concentrated to obtain 4-nonyl-2-methylphenyl acetate (1098.3 g) in 99.7% yield.

EXAMPLE 5

Preparation of 3-Methyl-2-hydroxy-5-nonylacetophenone (2b)

4-Nonyl-2-methylphenyl acetate (2a) (546.6 g, 1.98 mol) in acetic anhydride (302 mL) was treated with ethereal borontrifluoride (312 mL, 2.48 mol) at 105° C. for 4.5 h. Crude product dissolved in heptane was washed with water and brine until the pH of the washings became neutral. Thick amber liquid obtained from removal of the solvent was distilled to yield 3-methyl-2-hydroxy-5-nonyl-acetophenone in ca. 50% yield.

EXAMPLE 6

Preparation of 3-Methyl-2-hydroxy-5-nonylacetophenoxime (2c)

3-Methyl-2-hydroxy-5-nonylacetophenone (2b) (102.5 g, 0.37 mol) was treated with hydroxylamine sulfate (36.44 g, 0.22 mol) and anhydrous sodium acetate (36.44 g, 0.44 mol) in methanol (150 mL) at reflux for 7 h. Crude product in the solvent was filtered and concentrated. The resulting oxime was converted to copper(II) complex and purified further by flash column chromatography. Pure fractions were pooled and treated with aqueous 200 gpl sulfuric acid. Removal of the solvent gave 3-methyl-5-nonylsalicylaldoxime.

EXAMPLE 7

Preparation of 2-Isopropyl-4-nonylphenol (3a)

2-Isopropylphenol (272.6 g, 2.0 mol), tripropylene (131.74 g), and Amberlyst 15 (8.55 g) were stirred for 7 h at 125° C. Work-up and in vacuo distillation as given for 1b gave 2-isopropyl-4-nonylphenol (239.4 g, 96.4% purity by GC area %) in 46% yield.

EXAMPLE 8

Preparation of 3-Isopropyl-5-nonylsalicylaldehyde (3b)

2-Isopropyl-4-nonylphenol (3a) (239.4 g, 0.914 mol) in toluene (470 mL) was placed in a 4-neck RBF equipped with a thermometer, a condenser, and a mechanical stirrer. To the solution was added methanolic magnesium methoxide (685 mL of 7.4 wt. %, d. 0.816 g/mL). The methanol was distilled off gradually so that the pot temperature was raised to 100° C. Then solid paraformaldehyde (80 g, 2.7 mol) was introduced in portions for 30 mins. maintaining the same temperature. Crude product was distilled and further purified by flash column chromatography to obtain 3-isopropyl-5-nonylsalicylaldehyde (52.6 g) in 20% yield.

EXAMPLE 9

Preparation of 3-Isopropyl-5-nonylsalicylaldoxime (3c)

Oximation and workup of 3-isopropyl-5-nonylsalicylaldehyde (3b) (57.6 g, 0.2 mol) as described for 1c gave 3-isopropyl-5-nonylsalicylaldoxime (58.21 g) in 96.1% yield.

EXAMPLE 10

Preparation of 2-n-Propyl-4-nonylphenol (4a)

2-n-Propylphenol (5 mol, 681 g), dry Amberlyst 15 (50 g) and tripropylene (5.5 mol, 694 g, 951 ml) were placed in a 3000 ml 3N RBF. The mixture was heated and maintained at 120° C. under vigorous stirring for 7 hrs. After cooling to ambient temperature, the reaction mixture was filtered and distilled to obtain 2-n-propyl-4-nonylphenol in vacuo (135–150° C. at 0.5–2 T). Total 960 g of 2-n-propyl-4-nonylphenol was obtained as amber oils (71% yield with 95% plus purity).

EXAMPLE 11

Preparation of 3-n-Propyl-5-nonylsalicylaldehyde (4b)

A pressure reactor was charged with 500 ml of toluene and heated to 218° C. A slurry of a mixture of 2-n-propyl-4-nonylphenol (262 g, 1.0 mol) paraformaldehyde (94.5 g, 3.15 mol), titanium cresylate (2 ml) and 50 ml of toluene was added over 5 min. The container of slurry was washed two times with 2×50 ml of toluene. The reaction mixture was heated (the reactor was heated with a 250° C. hot oil circulating through internal coil) and stirred for 25 mins. and discharged from the reactor. The dark brown mixture was washed with 5% H2SO4 and water. The organic solution was separated and dried over MgSO4. Removal of the solvent left dark color oil as crude product. The purification was achieved through vacuums distillation and chromatography.

EXAMPLE 12

Preparation of 3-n-Propyl-5-nonylsalicylaldehydoxime (4c)

3-n-Propyl-5-nonylsalicylaldehyde (63.9 g, 0.22 mol), hydroxyamine sulfate (21.7 g, 0.13 mol) and sodium acetate (21.7 g, 0.26 mol) were mixed and 150 ml of MeOH was added. The mixture formed a suspension. The suspension was stirred and boiled under reflux until no starting material was left (indicated by TLC). The reaction mixture was filtered and the solid was washed with MeOH. The MeOH solution was combined. Removal of MeOH by rotovap left pale yellow oil as crude product that was dissolved in 250 ml of heptane. The heptane solution of the crude product was washed with water, sodium bicarbonate/water and water. The solution was dried over sodium sulfate and solvent was removed on rotovap. The desired product was obtained as pale yellow oil (66.4 g, 99% yield).

EXAMPLE 13

Preparation of 2-Methoxy-4-nonylphenol (5a)

2-Methoxyphenol (5 mol, 621 g), dry Amberlyst 15 (50 g) and tripropylene (5.5 mol, 694 g, 951 ml) were placed in a 3000 ml 3N RBF. The mixture was heated and maintained at 120° C. under vigorous stirring for 7 hrs. After cooling to ambient temperature, the reaction mixture was filtered and distilled to obtain 2-methoxy-4-nonylphenol in vacuo.

EXAMPLE 14

Preparation of 3-Methoxy-5-nonylsalicylaldehyde (5b)

A pressure reactor was charged with 500 ml of toluene and heated to 218° C. A slurry of a mixture of 2-methoxy-4-nonylphenol (250.4 g, 1.0 mol), paraformaldehyde (94.5 g, 3.15 mol), titanium cresylate (2 ml) and 50 ml of toluene was added over 5 mins. The container of slurry was washed two times with 2×50 ml of toluene. The reaction mixture was heated (the reactor was heated with a 250° C. hot oil circulating through internal coil) and stirred for 25 mins. and discharged from the reactor. The dark brown mixture was washed with 5% H2SO4 and water. The organic solution was separated and dried over MgSO4. Removal of the solvent left dark color oil as crude product. The purification was achieved through vacuums distillation and chromatography.

EXAMPLE 15

Preparation of 3-Methoxy-5-nonylsalicylaldehydoxime (5c)

3-Methoxy-5-nonylsalicylaldehyde (87.8 g, 0.32 mol), hydroxyamine sulfate (34 g, 0.21 mol) and sodium acetate (34 g, 0.32 mol) were mixed and 230 ml of MeOH was added. The mixture formed a suspension. The suspension was stirred and boiled under reflux until no starting material left (indicated by TLC). The reaction mixture was filtered and the solid was washed with MeOH. The MeOH solution was combined. Removal of MeOH by rotovap left pale yellow oil as crude product that was dissolved in 250 ml of heptane. The heptane solution of the crude product was washed with water, sodium bicarbonate/water and water. The solution was dried over sodium sulfate and solvent was removed on rotovap. The desired product was obtained as pale yellow oil.

EXAMPLE 16

Preparation of 2-Methyl-4-octylphenol (6a)

Iso-octenes (320.8 g, 2.625 mol) was reacted with o-cresol (270.3 g, 2.5 mol) in the presence of dry Amberlyst 15 (12.5 g) at elevated temperature (100–125° C.). Crude 4-octyl-2-cresol was distilled in vacuo to obtain 2-methyl-4-octylphenol (367.8 g) in 63% yield.

EXAMPLE 17

Preparation of 2-Methyl-4-octylphenyl Acetate (6b)

4-Octyl-2-cresol (6a) (245.51 g, 1.116 mol) was treated with acetic anhydride (149.3 g, 1.45 mol) in the presence of a few drops of concentrated sulfuric acid at 110° C. for 1.5 h. After cooling to ambient temperature, the reaction mixture was transferred into a 4-l separatory funnel with aid of heptane (400 mL). The resulting organic phase was washed with aqueous sodium bicarbonate solution and water until the pH became 6 or so. The heptane phase was dried over sodium sulfate and concentrated to obtain 4-nonyl-2-methylphenyl acetate (285.5 g) in 97.6% yield.

EXAMPLE 18

Preparation of 3-Methyl-2-hydroxy-5-octylacetophenone (6c)

4-Octyl-2-methylphenyl acetate (6b) (276 g, 1.0 mol) in acetic anhydride (102 g) was treated with ethereal borontrifluoride (157.3 mL, 1.25 mol) at 110–115° C. for 3 h. Crude product dissolved in heptane was washed with 200 gpl sulfuric acid, water and brine until the pH of the washings became neutral. Thick amber liquid obtained from removal of the solvent was distilled to yield 3-methyl-2-hydroxy-5-octylacetophenone in ca. 45% yield.

EXAMPLE 19

Preparation of 3-Methyl-2-hydroxy-5-octylacetophenoxime (6d)

3-Methyl-2-hydroxy-5-octylacetophenone (6c) (42.55 g, 0.1542 mol) was treated with hydroxylamine sulfate (15.8 g, 96.4 mmol) and anhydrous sodium acetate (15.8 g, 192.4 mmol) in methanol (100 mL) at reflux for 17 h. Crude product was purified following the procedure described for 2c to obtain 3-methyl-2-hydroxy-5-octylacetophenoxime.

EXAMPLE 20

In each step of the experiment, contacting of organic and aqueous phases were done by shaking in a separatory funnel for 10 mins. First, 50 ml each of fresh oxime (0.176 Molar) in Conoco 170E kerosene diluent and QC Electrolyte (35 g/L Cu, 160 g/L H2SO4) were contacted for 10 minutes. The aqueous phase was separated and the organic phase was filtered through phase separation paper [Eq Org]. Of the filtered organic phase, 45 ml was contacted with 45 ml of QC Feed (6.0 g/L Cu, 3.0 g/L Fe, pH 2.0). The organic phase was filtered [L Org], and 40 ml was contacted with 40 ml of QC Electrolyte again. The organic phase was filtered [S Org], and 35 ml was contacted with 35 ml of Performance Feed (2.5 g/L Cu, 4.0 g/L Fe, pH 1.6). The organic phase was filtered [PL Org], and 30 ml was contacted three times with 30 ml each time of Modifier Electrolyte (30.5 g/L Cu, 149 g/L H2SO4). The organic phase was filtered [ME Org], and 25 ml was contacted with 25 ml of Modifier Feed (5.9 g/L Cu, 5.6 g/L Fe, pH 1.5). The organic phase was filtered [ML Org], and 20 ml was contacted with 20 ml of Modifier Electrolyte again. The organic phase was filtered [MS Org]. Samples of organic from each filtration were analyzed by atomic adsorption for copper and iron concentration; results are tabulated under the headings indicated above in brackets. In the table, NT stands for Net Transfer, and is the difference in copper concentration between organic contacted with electrolyte and organic contacted with feed solution. Cu/Fe stands for the ratio of copper to iron concentrations in the loaded organic. The extraction data for each of the following oximes is given below: MA (3-methyl-2-hydroxy-5-nonylsalicylaldoxime); PA (3-propyl-2-hydroxy-5-nonylsalicylaldoxime); IA ((3-isopropyl-2-hydroxy-5-nonylsalicylaldoxime; MA+(MA+35 g/l of a mixture of succinic, glutaric and adipic acids esterified with a $C_{6-8}$ fatty alcohol); MeOA ((3-methoxy-2-hydroxy-5-nonylsalicylaldoxime); MK (3-methylyl-2-hydroxy-5-nonyl acetophenone oxime).

What is claimed is:

1. A process for the separation of copper from iron in an aqueous feedstock solution containing dissolved copper and iron values comprising contacting the feedstock solution with a water-immiscible organic solution comprised of a hydrocarbon solvent and a compound of the formula I

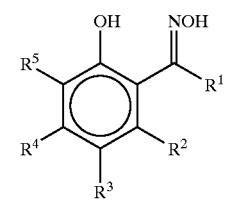

wherein $R_5$ is a $C_{1-22}$ linear or branched alkyl group; R1 is hydrogen, or a $C_{1-22}$ linear or branched alkyl or alkenyl group, a $C_6$ aryl group or a $C_{7-22}$ aralkyl group; $R_2$–$R_4$ is hydrogen, halogen, a linear or branched $C_{6-12}$ alkyl group, $OR_6$ wherein $R_6$ is a $C_{1-22}$ linear or branched alkyl group, a $C_{2-22}$ linear or branched alkenyl group, a $C_6$ aryl group, or a $C_{7-22}$ aralkyl group to form an aqueous phase comprised of iron and an organic phase comprised of the hydrocarbon solvent and a copper-extractant complex wherein the copper-extractant complex is soluble in the hydrocarbon solvent.

Aldoximes

| Assay | | ML | Eq Org | L Org | QC NT | QC Cu/Fe | S Org | PL Org | PF NT | PF Cu/Fe | ME Org | ML Org | MS Org | M NT | M Cu/Fe |
|---|---|---|---|---|---|---|---|---|---|---|---|---|---|---|---|
| 860N | Cu | 5.70 | 2.89 | 5.33 | 2.44 | 2280 | 3.21 | 5.03 | 1.82 | 295 | 2.99 | 5.34 | 3.16 | 2.35 | 2098 |
|  | Fe |  | 0 | 0.00107 |  |  | 0 | 0.00617 |  |  | 0 | 0.00112 | 0 |  |  |
| MA | Cu | 5.51 | 3.54 | 5.35 | 1.81 | 18100 | 3.80 | 5.24 | 1.44 | 3600 | 3.73 | 5.34 | 3.85 | 1.61 | 16100 |
|  | Fe |  | 0 | 0.00010 |  |  | 0 | 0.00040 |  |  | 0 | 0.00010 | 0 |  |  |
| PA | Cu | 5.60 | 3.30 | 5.51 | 2.21 | 221000 | 3.67 | 5.34 | 1.67 | 1415 | 3.48 | 5.51 | 3.58 | 2.03 | 203000 |
|  | Fe |  | 0 | 0.00010 |  |  | 0 | 0.00118 |  |  | 0 | 0.00001 | 0 |  |  |
| IA | Cu | 5.60 | 2.67 | 5.41 | 2.74 | 19571 | 2.98 | 4.99 | 2.01 | 450 | 2.74 | 5.36 | 2.85 | 2.62 | 10480 |
|  | Fe |  | 0 | 0.00014 |  |  | 0 | 0.00447 |  |  | 0 | 0.00025 | 0 |  |  |
| MA+ | Cu | 5.45 | 2.74 | 5.27 | 2.53 | 84333 | 3.12 | 4.92 | 1.80 | 4186 | 2.89 | 5.20 | 3.01 | 2.31 | 46200 |
|  | Fe |  | 0.00000 | 0.00003 |  |  | 0.00000 | 0.00043 |  |  | 0.00000 | 0.00005 | 0.00000 |  |  |
| MeOA | Cu | 5.60 | 5.13 | 5.60 | 0.47 |  | 5.23 | 5.66 | 0.43 |  | 5.21 | 5.63 | 5.25 | 0.42 |  |

\+ - plus Emery ester

Ketoximes

| Assay | | ML | Eq Org | L Org | QC NT | QC Cu/Fe | S Org | PL Org | PF NT | PF Cu/Fe | ME Org | ML Org | MS Org | M NT | M Cu/Fe |
|---|---|---|---|---|---|---|---|---|---|---|---|---|---|---|---|
| 84-IC | Cu | 5.55 | 0.29 | 4.15 | 3.86 | 2339 | 0.33 | 2.45 | 2.12 | 337 | 0.28 | 3.77 | 0.33 | 3.49 | 2053 |
|  | Fe |  | 0 | 0.00165 |  |  | 0 | 0.00629 |  |  | 0 | 0.00170 | 0 |  |  |
| MK | Cu | 5.51 | 0.45 | 4.43 | 3.98 | 398000 | 0.56 | 2.70 | 2.14 | 1196 | 0.43 | 4.14 | 0.51 | 3.71 | 61833 |
|  | Fe |  | 0 | 0.00001 |  |  | 0 | 0.00179 |  |  | 0 | 0.00006 | 0 |  |  |

MA - Methyl Aldoxime
QC Feed -6.0 g/l Cu, 3.0 g/l Fe, pH = 2.0
MK - Methyl Ketoxime
QC Electrolyte -35.0 g/l Cu, 160 g/l $H_2SO_4$
PA - n-Propyl Aldoxime
PF Feed -2.5 g/l Cu, 4.0 g/l Fe, pH = 1.6
IA - Isopropyl Aldoxime
M Feed - 5.9 g/l Cu, 5.6 g/l Fe, pH = 1.5
MeOA - Methoxy Aldoxime
M Electrolyte -30.5 g/l Cu, 149 g/l $H_2SO_4$ 2. The process of claim 1 wherein each of $R_1$, $R_2$ and $R_4$ is hydrogen, $R_5$ is methyl, and $R_3$ is nonyl.

3. The process of claim 1 wherein $R_1$ is hydrogen, $R_5$ is methyl, and one of $R_2$–$R_4$ is nonyl.

4. The process of claim 1 wherein each of $R_1$, $R_2$ and $R_4$ is hydrogen, $R_5$ is n-propyl, and $R_3$ is nonyl.

5. The process of claim 1 wherein each of $R_1$, $R_2$ and $R_4$ is hydrogen, $R_5$ is iso-propyl, and $R_3$ is nonyl.

6. The process of claim 1 wherein each of $R_2$ and $R_4$ is hydrogen, $R_5$ is methyl, $R_1$ is phenyl and $R_3$ is octyl.

7. The process of claim 1 further comprising the step of separating the organic phase from the aqueous phase.

8. The process of claim 1 wherein the aqueous feedstock is a concentrate leach or a bioleach solution.

* * * * *